Figure 7:
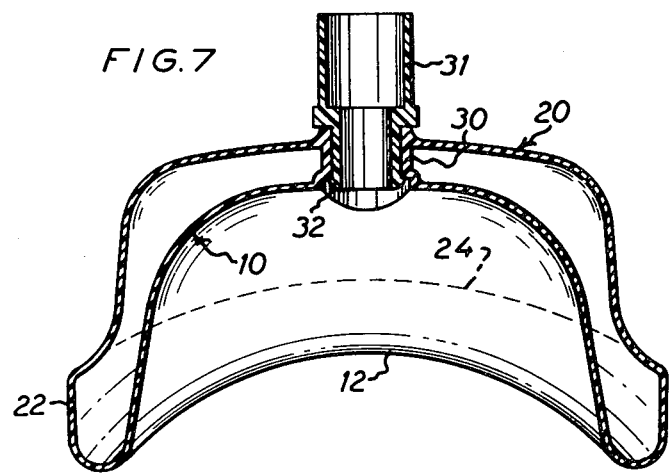

United States Patent [19]
Halldin et al.

[11] 3,982,532
[45] Sept. 28, 1976

[54] BREATHING MASK, PARTICULARLY FOR ARTIFICIAL RESPIRATION

[75] Inventors: Matts Arne Bernhard Halldin, Lidingo; Nils Rune Gustaf Andréasson, Stockholm, both of Sweden

[73] Assignee: Gnosjoplast AB, Gnosjo, Sweden

[22] Filed: Dec. 17, 1974

[21] Appl. No.: 533,497

[30] Foreign Application Priority Data
Dec. 19, 1973 Sweden .............................. 7317152

[52] U.S. Cl. ................................ 128/146; 128/205
[51] Int. Cl.² .......................................... A62B 18/02
[58] Field of Search ............... 128/140 R, 146, 141, 128/146.3–146.5, 146.7, 188, 195, 205, 145.8

[56] References Cited
UNITED STATES PATENTS

| | | | |
|---|---|---|---|
| 2,254,854 | 9/1941 | O'Connell | 128/205 |
| 2,313,999 | 3/1943 | Kreiselman | 128/205 |
| 2,998,818 | 9/1961 | Tabor et al. | 128/205 |

FOREIGN PATENTS OR APPLICATIONS

| | | | |
|---|---|---|---|
| 552,798 | 2/1958 | Canada | 128/146 |
| 6,085 | 3/1913 | United Kingdom | 128/205 |

*Primary Examiner* — William E. Kamm

[57] ABSTRACT

Breathing mask of double-wall construction having a relatively rigid outer wall and an inner wall with deformable sealing pads to be pressed against either side of the nose and the adjoining portions of the cheeks and with a rigid arc-shaped portion to be pressed against the chin.

2 Claims, 8 Drawing Figures

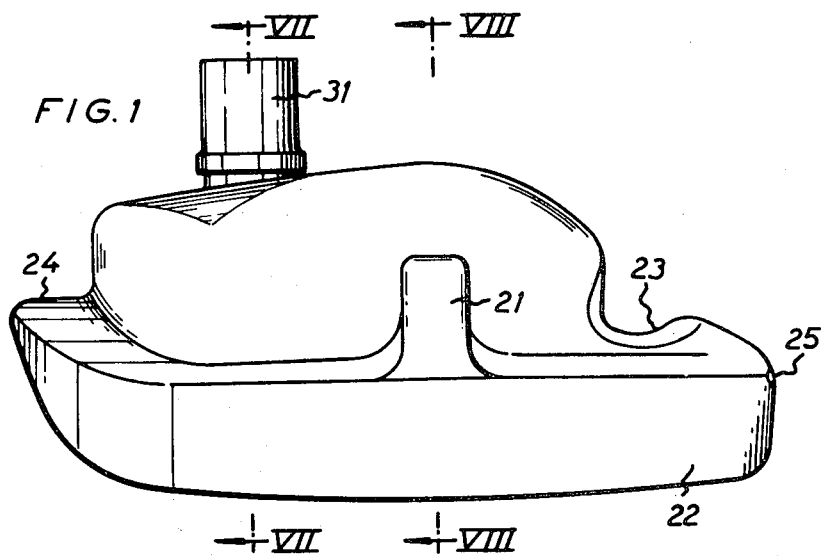
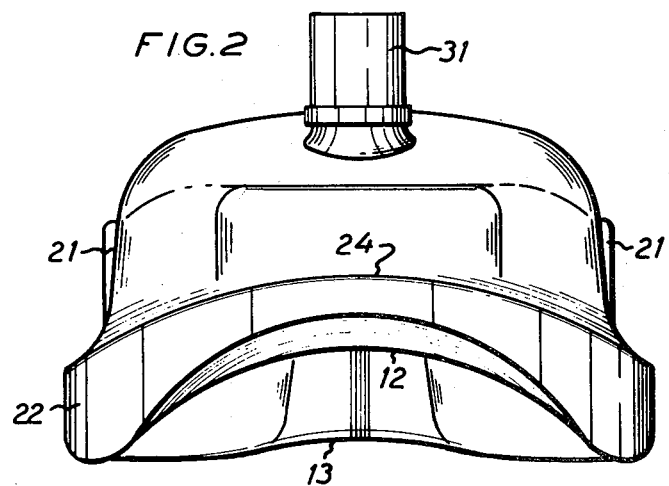

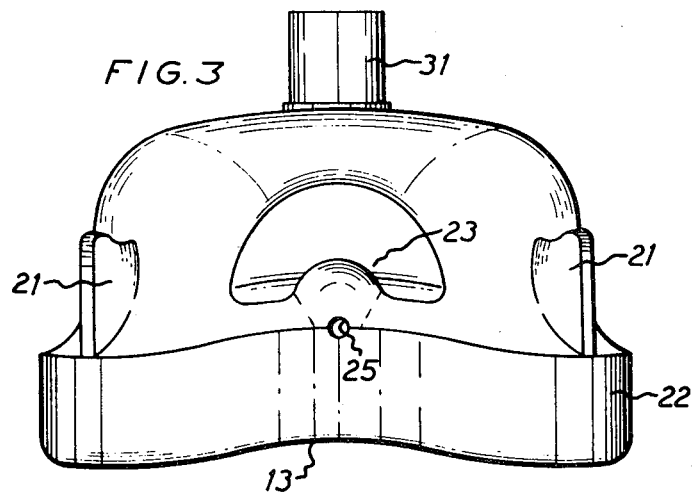
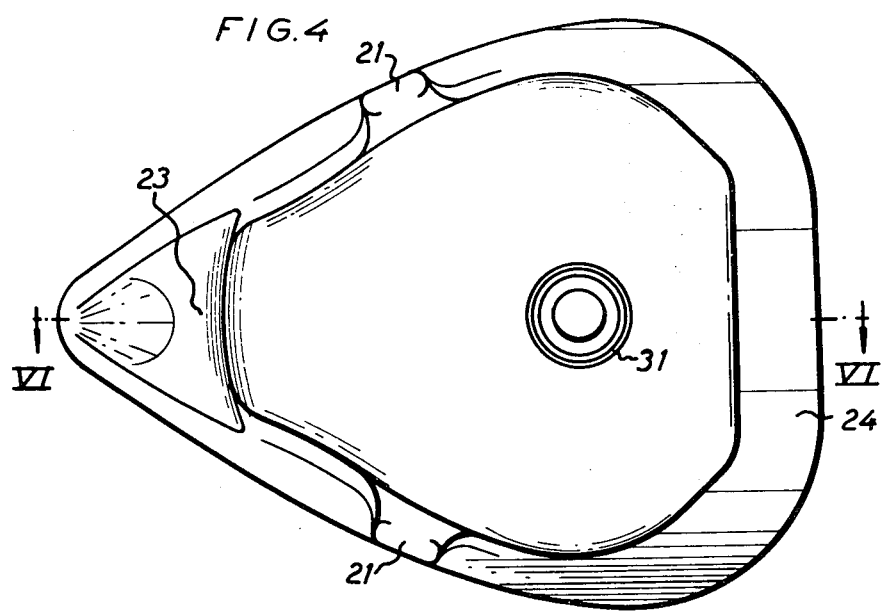

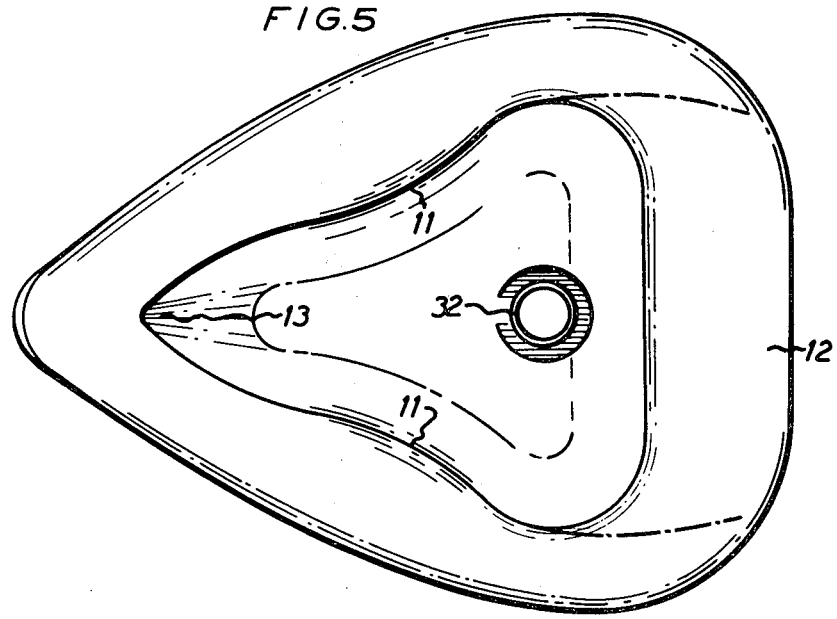
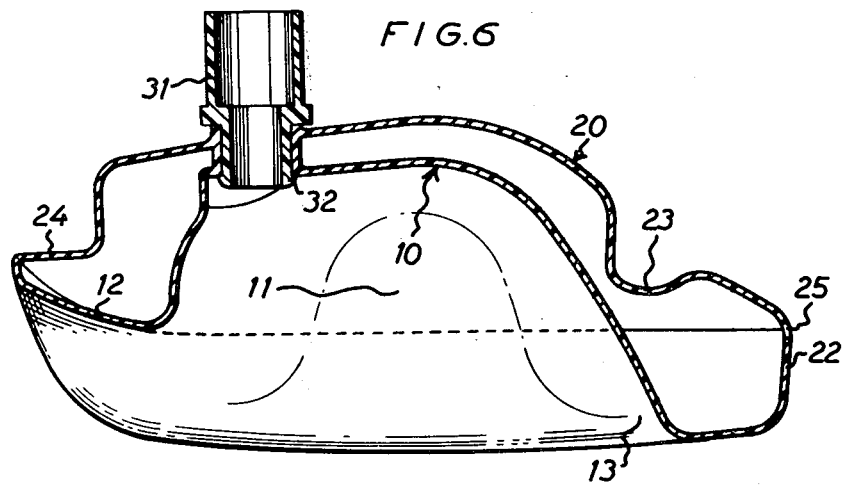

BREATHING MASK, PARTICULARLY FOR ARTIFICIAL RESPIRATION

The present invention relates to a breathing mask, particularly for artificial respiration, said mask comprising a face piece designed to be pressed against the area surrounding the mouth and the nose in a sealing fashion and having a combined inlet and outlet opening for breathing gas.

In conjunction with the administration of anaesthetics and respirator ventilation of patients it is previously known to use a mask consisting of a face piece which can be pressed in a sealing fashion against the area surrounding the mouth and the nose, said face piece having a combined inlet and outlet opening for breathing gas. Previously known breathing masks used for such purposes are not, however, very well suited for use in connexion with artificial breathing according to the mouth-to-mouth method or in conjunction with ventilation by ballooning of unconscious persons.

An object of the present invention is to provide a breathing mask which is well suited for such purposes and, furthermore, is easy to mass-produce at a low cost, such that it may be included in the standard equipment of e.g. vehicles and pleasure boats.

Another object of the present innvention is to provide a breathing mask which has means for facilitating the handling and the attachment of the mask in connexion with artificial breathing according to the mouth-to-mouth method or in connection with ventilation by ballooning of unconscious persons.

According to the present invention, the breathing mask comprises a face piece which is made up of a double-wall construction of semi-soft to semi-rigid plastics or rubber material, said face piece having an inner wall with deformable sealing pads to be pressed against either side of the nose and the adjoining portions of the cheeks and with a rigid arc-shaped portion to be pressed against the chin and possibly the lower lip, and more rigid outer wall connected to said inner wall at the outer edge of the face piece and preferably forming one piece with said inner wall.

In a further development of the face piece, the outer wall thereof may be provided with reinforcing shoulders, preferably in the form of gripping surfaces and/or attachments for bands by which to fasten the breathing mask against the face.

Figure 8:
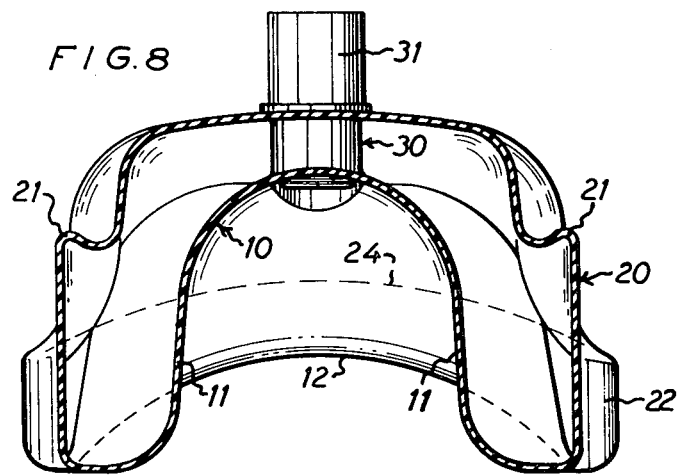

A particularly advantageous embodiment of the face piece according to the invention will be described in greater detail hereinbelow and with reference to the accompanying drawings, in which:

FIG. 1 shows the breathing mask in side elevation;
FIG. 2 shows the mask as viewed from one end;
FIG. 3 shows the mask as viewed from the other end;
FIG. 4 illustrates the breathing mask as viewed from above;
FIG. 5 illustrates the same mask as viewed from below;
FIG. 6 is a sectional view taken along the line VI—VI in FIG. 4;
FIGS. 7 and 8 are sectional views taken along the lines VII—VII and VIII—VIII, respectively, in FIG. 1.

As shown in the drawings, the breathing mask is a double-wall construction with one inner wall 10 and one outer wall 20. Said two walls are connected with each other, both at the outer edge of the mask and at a central pipe socket 30, in which a connecting piece 31 is inserted and retained by means of a circumferential embossment 32, acting as a spring catch together with the socket 30.

As will appear from the drawings, the breathing mask has been designed with particular respect to its operating position around the mouth and the nose, the pointed portion of the mask being placed over the nose and the wider portion thereof pressed against the chin or the lower lip to maintain the mouth open. In order to obtain the sealing pressure effect of the mask against the face and at the same time impart to the mask sufficient strength to permit transmission of the necessary pressure against the chin, the outer wall 20 of the mask has been so configured as to promote the elasticity of the mask but still has been made relatively rigid by means of reinforcing shoulders or projections 21. Furthermore, as the mask is pressed against the face, the lower edge 22 of the outer wall is oriented substantially perpendicularly to the face, the sealing effect of the mask thereby being further enhanced. The pipe socket 30, extending between the inner wall 10 and the outer wall 20, also has a reinforcing effect on the mask. To facilitate the handling and retention of the breathing mask the outer wall has been formed with additional gripping surfaces 23, 24.

In order to facilitate the sealing operation between the mask and the face, the inner wall 10 of the face piece has been provided with deformable sealing pads 11, being so shaped that they will be pressed in a sealing fashion against either side of the nose and the adjoining portions of the cheeks. The internal space between the inner and the outer wall communicates with the ambient air via a small aperture 25 formed at the pointed portion of the mask. By such a ventilation arrangement, it will be easier to press the mask against the face and also possible to deform the outer wall to some extent and thus affect the pressure of the inner wall against the face.

The inner wall 10 also has a rigid arc-shaped portion 12 to be pressed against the chin and possibly against the downwardly folded lower lip, whereby it will become easier to assure that the mouth of the person subjected to the artificial respiration is maintained open. At the other end of the mask the inner wall tapers into a pointed portion at 13 so as to fit over the nose, said pointed portion being also somewhat arched upwardly, as will best appear from FIGS. 2 and 3. It will thus be possible to enhance the effect of the pressure exerted by those portions of the outer wall 20, which are located on a level with the reinforcing shoulders 21, against the face on either side of the nose.

The reinforcing shoulders 21 are in the form of small hooks, such that the mask can be secured against the face, for instance by means of a doubled rubber band, being first passed over and fixed on one shoulder 21 and then pulled down behind the back of the neck of the patient, to be hooked onto the shoulder 21 on the opposite side of the mask. It is also possible to apply additional rubber bands to the gripping surfaces 23 and 24. Applying the breathing mask in this way may be particularly advantageous when the spontaneous respiration has commenced and it is desirable to support the respiration by means of oxygen, being supplied via the connecting piece 31 which preferably is of standard dimensions so as to fit the ordinary equipment of ambulances and hospitals.

As mentioned above, the breathing mask is made of a semi-soft to semi-rigid plastics or rubber material. A particularly advantageous material is polyvinyl chloride, which may readily be brought into the required shape by blow moulding. For this reason, the breathing mask is well suited for mass production at a low cost.

What we claim and desire to secure by Letters Patent is:

1. An integral breathing mask, particularly for artificial respiration, comprising an inner and outer wall of resilient material, the circumferential edges of said walls being connected to define a cup-shaped face mask having a variable volume internal air space therebetween and generally designed to surround the nose and mouth of the patient in a sealing manner, said outer wall being provided with a continuously open vent for venting the internal air space between the inner and outer resilient walls to the atmosphere, said inner and outer walls being connected at a point removed from the circumferential edges thereof to provide a tubular passage for admitting a breathing gas to the inside of the mask, said resilient outer wall being provided with a circumferential wall portion extending substantially perpendicular to the surface of the patient's face, and deformable resilient sealing pads formed on the inside of the inner wall for pressing against the sides of the nose and adjoining cheek portions of the patient, said inner wall having a rigid arcuate portion adjacent its circumference for pressing against the chin area of the patient, and said outer wall having opposed reinforced portions adjacent the circumferential wall portion for gripping and handling the mask.

2. A breathing mask as claimed in claim 1 wherein said tubular passage includes inner and outer abutment surfaces for resiliently engaging a conduit for admitting a breathing gas.

* * * * *